(12) United States Patent
Scherkowski et al.

(10) Patent No.: US 9,974,566 B2
(45) Date of Patent: May 22, 2018

(54) HAND-HELD DEVICE FOR PIERCING A HUMAN OR ANIMAL SKIN, AND NEEDLE MODULE

(71) Applicant: MT.DERM GmbH, Berlin (DE)

(72) Inventors: Dirk Scherkowski, Berlin (DE);
Kornelius Knothe, Berlin (DE);
Andreas Loth, Berlin (DE)

(73) Assignee: MT.DERM GmbH, Berlin (DE)

( * ) Notice: Subject to any disclaimer, the term of this patent is extended or adjusted under 35 U.S.C. 154(b) by 1339 days.

(21) Appl. No.: 13/936,122

(22) Filed: Jul. 5, 2013

(65) Prior Publication Data
US 2014/0018835 A1   Jan. 16, 2014

(30) Foreign Application Priority Data

Jul. 12, 2012   (EP) ..................................... 12175114

(51) Int. Cl.
*A61B 17/34* (2006.01)
*A61M 5/46* (2006.01)
*A61M 37/00* (2006.01)
*A61M 5/32* (2006.01)

(52) U.S. Cl.
CPC .......... *A61B 17/3494* (2013.01); *A61M 5/46* (2013.01); *A61M 37/0076* (2013.01); *A61M 5/3287* (2013.01); *A61M 5/3293* (2013.01); *A61M 5/3298* (2013.01)

(58) Field of Classification Search
CPC .... A61B 17/3494; A61B 5/150175–5/150198; A61M 5/46; A61M 37/0076; A61M 5/3298; A61M 5/3293; A61M 5/3287; A01K 11/005
See application file for complete search history.

(56) References Cited

U.S. PATENT DOCUMENTS

| | | | |
|---|---|---|---|
| 4,990,135 A | 2/1991 | Truesdale, Jr. | |
| 6,558,402 B1* | 5/2003 | Chelak | A61B 5/1411 600/583 |
| 2012/0271335 A1* | 10/2012 | Lee | A61M 37/0084 606/185 |

FOREIGN PATENT DOCUMENTS

| | | |
|---|---|---|
| EP | 1992387 A2 | 11/2008 |
| EP | 2388033 A1 | 11/2011 |

(Continued)

OTHER PUBLICATIONS

Extended European Search Report, directed to EP Patent Application No. 12175114.3, dated Feb. 18, 2013, 10 pages.

*Primary Examiner* — Shaun L David
(74) *Attorney, Agent, or Firm* — Leason Ellis LLP

(57) ABSTRACT

A hand-held device for piercing a human or animal skin, comprises a housing, a drive device, which is arranged in the housing and is suitable for repeatedly providing a feed motion. The device also comprises a piercing device, which is formed in the housing with a needle and is coupled directly or, via a coupling device, indirectly to the drive device in such a way that the feed motion provided by the drive device can be introduced onto the piercing device. There is a housing opening, relative to which the needle moves forwards and backwards during operation, and a piercing depth adjuster, which is coupled to the piercing device in such a way that the piercing depth adjuster is displaceable relative to the tip of the needle and is entrained with the needle as the needle moves forwards/backwards during operation.

15 Claims, 3 Drawing Sheets

(56) References Cited

FOREIGN PATENT DOCUMENTS

| EP | 2454966 A2 | 5/2012 |
|----|------------|--------|
| WO | 2012029082 A1 | 3/2012 |

\* cited by examiner

HAND-HELD DEVICE FOR PIERCING A HUMAN OR ANIMAL SKIN, AND NEEDLE MODULE

The invention relates to a hand-held device for piercing a human or animal skin and also to a needle module for such a hand-held device.

BACKGROUND OF THE INVENTION

Various embodiments of hand-held devices are provided for piercing for puncturing a human or animal skin. A substance may be introduced into the skin or underlying tissue in conjunction with the piercing process. Such an introduction takes place for example when using a syringe as a hand-held device, with a substance to the applied being introduced through the cannula of the syringe after the piercing operation. The introduction of a substance into the skin also takes place in conjunction with the production of tattoos or permanent makeup. In this case, the skin is punctured in order to then introduce an ink into the skin layers. In conjunction with other medical or cosmetic applications however, it may also be that a substance, for example a cosmetic or a medical active ingredient, is introduced into the skin and/or underlying tissue in conjunction with the piercing process. One field of application in this area is mesotherapy.

Different substances often require a different piercing depth when piercing the needle of the hand-held device into the skin. For example, the effect to be developed of the introduced substance can be optimised by means of a suitable piercing depth. A further action is the stimulation of the skin by means of piercing the skin, for example for the treatment of wrinkles or for the treatment of scars. These treatments can also be carried out without the insertion of any substance. The capacity to adjust the piercing depth is of significance here in order to reach the desired skin layer. If the piercing is too shallow, the desired results will not be provided. If the piercing is too deep, excessive trauma will be caused.

To vary the piercing depth, it has been proposed for example to vary the stroke performed by the needle of the hand-held device. The length via which the needle protrudes with respect to a front housing opening, for example the opening in a needle jet, at the end of the extension movement is then adjustable as a result. This type of piercing depth adjustment requires an adjustment mechanism for stroke adjustment and is therefore routinely complex.

In the case of tattoo and permanent makeup devices, a needle protrusion can also be adjusted by changing the distance between a front needle jet opening and the needle tip in the extended position of the needle. In document EP 2 388 033 A1 it has been proposed, similarly to this principle, to arrange an attachment part on a syringe that is to be manually actuated, the axial length of the attachment part being adjustable by fitting a front component via a screw thread onto a base component, such that, by means of rotation of the front component, the length of the attachment part is adjusted on the whole. The length of the cannula by which the cannula protrudes beyond the distal end of the attachment part is thus ultimately adjusted. The piercing depth for the cannula of the syringe can thus be adjusted. The adjustment of different lengths of the attachment part means that the front part and the base part are mechanically coupled to one another to a different extent. The region of overlap between the front part and the base part is shorter, the further the front part is unscrewed in order to reduce the piercing depth. The reduction of the overlap between the two components is not advantageous for the mechanical stability of the connection between the components.

A tattoo device is known from document EP 2 454 966 A2, in which a stroke performed by the piercing needle is adjustable. To this end, recesses offset from one another in the axial direction are provided on a connecting rod and a protrusion on the needle shaft engages into the recesses, wherein different needle strokes are implemented by means of engagement in different recesses. The piercing depth changes according to the needle stroke.

A hand-held tattoo device is also known from document EP 1 992 387 A2. Documents U.S. Pat. No. 4,990,135, WO 2012/029082 A1 and also EP 2 388 033 A1 relate to syringes with which a needle length protruding beyond the front housing tip is variable.

SUMMARY OF THE INVENTION

It is an object to provide a hand-held device for piercing a human or an animal skin, in which a piercing depth can be easily adjusted in a versatile manner. The adjustability of the piercing depth is to be usable in different types of piercing devices.

According to an aspect, a hand-held device for piercing a human or animal skin is provided in such a way that underlying tissue can also be reached selectively. In a housing, which is preferably formed with a number of parts or pieces with separable housing parts, a drive device is arranged, which is suitable for repeatedly providing a feed or drive motion. The drive device can be a manual or a motor-driven drive device. It is characteristic that a feed force is repeatedly provided with the aid of the drive device and is then coupled directly or via an intermediate coupling device onto a piercing device in order to repeatedly extend a needle comprised by the piercing device. In the case of the motor-driven drive device, an electric motor can be used for example in order to provide a feed force multiple times. This can occur in a repeating or oscillating manner, wherein the repetition frequency of the feed motion is variable in one embodiment. Motor-driven drive devices of this type or also other drive devices, for example pneumatic drives, are used for example in hand-held devices to form a tattoo or permanent makeup. Motor-driven or other drives for the hand-held device can also be used however in conjunction with the introduction into the skin and/or underlying tissue of other substances, whether these are medical or cosmetic active ingredients for example. Various embodiments of drive devices of this type are known as such.

The feed or drive motion provided by the drive device is coupled in onto a piercing device that is formed in the housing with a needle, which can also be referred to as a piercing element or piercing means. The drive or feed motion can be coupled in directly onto the piercing device or indirectly via an intermediate coupling device.

Additionally or alternatively, a restoring mechanism can be provided in order to retrieve the needle again after the extension, for example a spring mechanism and/or a membrane mechanism. During operation, the needle and, selectively, additionally components coupled to the needle moves/move towards the housing opening and away therefrom, wherein the housing opening is formed for example on a needle jet. The relative displacement of the needle can occur such that, at least in a fully extended position of the needle, the tip (piercing element tip) thereof protrudes in a forwards direction at the opening.

A piercing depth adjuster surrounding the needle completely or partially is coupled to the piercing device in such a way that the piercing depth adjuster is displaceable relative to the needle tip, preferably in the axial direction of the needle, and is entrained with the needle as the needle moves forwards and backwards during operation. This preferably means that the relative position of the piercing depth adjuster and needle tip does not change as the needle moves forwards and backwards during operation, since this distance was set beforehand. It can be changed by means of displacement of the piercing depth adjuster, in particular by means of axial displacement, in order to then function during subsequent operation with an amended piercing depth. In this case, no change of the stroke provided by the drive device is necessary, although this can be provided in addition. Rather, the piercing depth is determined by the relative position of the piercing depth adjuster with reference to the needle tip (free needle length), whereupon both are moved jointly during operation in accordance with the stroke provided by the drive device. In this regard, the free needle length specifies a needle protrusion with reference to the piercing depth adjuster, specifically the forwards-facing end thereof. This protrusion can be changed by means of displacement of the piercing depth adjuster.

The term "needle" in the meaning used here is used generally for different types of piercing elements or piercing tools that are suitable for piercing a skin and, as required, for piercing through a skin, and selectively also an underlying tissue portion, including the following designs in particular; single needle, needle bundle, single cannula, cannula bundle or cannula group, and also needle plate. The needles may be straight or curved with regard to their longitudinal extent. In the case of a needle plate, a plurality of needles or needle bundles are arranged at a distance from one another on the front face of a needle plate extending in a planar manner. These needles or needle bundles on the needle plate move together during operation relative to the opening of the needle jet, specifically towards the opening and away therefrom. In this case, at least the needle tips preferably protrude on the front face from the area of the opening of the needle jet in the extended position, such that the skin is pierced at least in part outside the needle jet. Alternatively, the needle tip may also still be arranged behind the opening in the needle jet in the extended position, that is to say it may still be arranged in the needle jet. In this case, the skin is pierced when the skin surface arches into the opening in the needle jet towards the needle tip, whether for example due to the placement of the needle jet onto the skin and/or due to a suction effect that is produced in the needle jet by means of the application of a vacuum. The piercing depth adjuster likewise moves with the needle plate during the extension and retraction.

In cases where cannulas are used, an active ingredient is injected through the cannula(s) into the skin or underlying tissue. There is then a fluidic connection to components that are used to apply pressure and to control the delivery of the active ingredient. Various embodiments of such fluid arrangements and components are known as such.

In the case of the hand-held device, the needle jet forms a front portion of the housing, which is arranged selectively detachably on the housing, with the opening, through which the needle selectively exits during operation.

Furthermore, a needle module or piercing element module for a hand-held device for piercing a human or animal skin is provided, in which a coupling portion for coupling to a drive device and also a piercing device are formed on a module housing and can be coupled directly or, via a coupling device, indirectly to the drive device in such a way that a feed motion provided repeatedly by the drive device can be introduced onto the piercing device. In a front opening on the housing, the needle and components coupled thereto selectively, such as the piercing depth adjuster, move forwards and backwards during operation. The opening is selectively formed by means of a needle jet or piercing element jet on the module housing. The needle jet or piercing element jet can be received detachably on the module housing.

A piercing depth adjuster is coupled to the needle device or piercing element device in such a way that the piercing depth adjuster is displaceable in the axial direction of the needle (of the piercing element) relative to the tip of the needle and is entrained with the forwards/backwards motion of the needle during operation.

The needle or piercing element module can be formed as a disposable module in order to be coupled to the drive device for use and removed and disposed of after use. The disposable module is preferably packed in a sterile manner.

A needle or piercing element module for a hand-held device for piercing a human or animal skin may be provided, comprising:
a module housing,
a coupling portion, which is formed on the module housing in order to be coupled to a housing of a drive device,
a piercing device, which is formed in the module housing with a needle and can be coupled directly or, via a coupling device, indirectly to the drive device in such a way that a feed motion provided by the drive device can be introduced onto the piercing device,
a housing opening, relative to which the needle moves forwards and backwards during operation, and
a piercing depth adjuster, which is coupled to the piercing device in such a way that the piercing depth adjuster is displaceable relative to the tip of the needle, preferably in the axial direction of the needle, and is entrained with the needle during the forwards/backwards motion of the needle during operation.

The needle may move forwards and backwards in the housing opening during operation, wherein the needle tip can pass through the opening in this case.

The needle may be received on a needle carrier, which is coupled directly or, via the coupling device, indirectly to the drive device. The needle carrier or piercing element carrier may for example comprise a needle shaft (piercing element shaft), in which the needle is received. In the case of the embodiment of the piercing device with a needle plate, this is received on the needle carrier, preferably so as to be tiltable transversely to the axial direction of the needle device. In the case of the direct coupling of the piercing device to the drive device, the needle carrier may form a type of intermediate piece between the drive device and the piercing device. In accordance with one embodiment, the needle carrier can be formed as part of the coupling device for the indirect coupling between the drive device and the piercing device.

The piercing depth adjuster may be received on the needle so as to be displaceable in the axial direction. In this embodiment, the piercing depth adjuster can be arranged on the needle. Alternatively, the piercing depth adjuster can be mounted on the needle carrier. A joint mounting of the piercing depth adjuster on the needle and on the needle carrier may also be provided. In the case of the use of a needle plate, the piercing depth adjuster can be coupled for example to the needle plate, for example via a screw thread, which runs along the periphery of the needle plate and is used to adjust the piercing depth adjuster.

The piercing depth adjuster may be received on the needle on a needle ram or piercing element ram so as to be displaceable in the axial direction. In one embodiment, the needle ram sits fixedly on the needle and forms the base for the coupling of the piercing depth adjuster thereto, which in turn is mounted on the needle ram.

The piercing depth adjuster may be coupled to the piercing device via a rotary adjustment mechanism. A rotary adjustment mechanism is produced for example by means of a screw thread in such a way that components involved in the rotary adjustment mechanism are positioned relative to one another by means of rotation. For example, in accordance with one embodiment, the needle ram may be provided with an outer thread, onto which the piercing depth adjuster is screwed in such a way that, by rotating the piercing depth adjuster, the position thereof relative to the needle ram and therefore to the needle can be adjusted in the axial direction of the needle. By means of rotation, the piercing depth adjuster is displaced in this case more closely towards the needle tip or away therefrom.

The housing opening may be formed on a needle jet. In the case of the hand-held device, a needle jet forming a front housing portion is then provided for example and comprises an opening in which the needle (the piercing element) of the piercing device and components selectively coupled thereto, such as the piercing depth adjuster, move forwards and backwards during operation. In accordance with this or other embodiments, the needle, even when moving back, can be forcibly guided by the drive device, at least in portions, over the traveled path by coupling a restoring force from the drive device onto the needle.

A guide element formed on the piercing depth adjuster may be assigned a guide formed on the needle jet, the guide element being guided in the guide as the needle moves forwards/backwards during operation. In accordance with one embodiment, one or more radially protruding guide elements are formed on the piercing depth adjuster and each engage in a respective assigned guide groove, which is formed in the needle jet. A distal end of the guide in the needle jet may form an extension limit for the piercing depth adjuster and therefore for the extension motion of the needle.

A needle jet housing component of the needle jet may be arranged displacably on the housing and can be functionally coupled to the piercing depth adjuster in such a way that, by means of displacement of the needle jet housing component, the piercing depth adjuster is displaced in the axial direction relative to the needle tip. For example, a displacement or a rotation of the needle jet component or of the entire needle jet due to the functional coupling thereto of the piercing depth adjuster can be used to axially displace the piercing depth adjuster relative to the needle tip.

The needle jet component may be arranged rotatably on the housing. In accordance with this embodiment, the piercing depth adjuster may be entrained in the event of rotation of the needle jet housing component, and the axial relative position of the piercing depth adjuster with respect to the needle tip is thus changed due to a threaded connection of the piercing depth adjuster to the needle or the needle carrier in order to thus perform a piercing depth adjustment.

At least a distal end of the piercing depth adjuster may surround the needle at least in some portions. The needle or the piercing element can be surrounded by the piercing depth adjuster in the region of the distal end thereof either continuously or in an interrupted manner. For example, in one embodiment, the piercing depth adjuster is embodied as a type of sleeve, through which the needle is guided. In this embodiment, the piercing depth adjuster surrounds the needle preferably along the entire length thereof. The shape, size and dimensions of the piercing depth adjuster are adaptable to the respective encompassed needle and also to the desired accuracy when defining the piercing depth. The distal end of the piercing depth adjuster may have a reversed funnel shape. The shaping in this case can emulate a tissue dent occurring when the skin is pierced.

The distal end of the piercing depth adjuster may have a tapering end portion. The taper is formed in the direction of the opening assigned to the needle tip. For example, a conical or cone-like end portion is formed by means of the taper.

A distal end face of the piecing depth adjuster may form, in an operating position, a common stop face with a front end face of the needle jet. In this case, the common stop face may have a conical design, to which the end face of the piercing depth adjuster on the one hand and the front end face of the needle jet on the other hand contribute.

The needle device, the needle jet and the piercing depth adjuster may be formed on a needle or piercing element module, which is arranged detachably on the housing. The needle module can be formed as a disposable module. It is preferably sealed on the rear face, that is to say on the side facing towards the drive device, in such a way that a liquid coming into contact with the needle in the needle jet cannot exit from the needle module on the rear face and cannot reach the drive device. Parts of the coupling device can be integrated selectively into the needle module. In order to seal the needle module on the rear face, a membrane formed from a resilient material may be used, which is preferably U-shaped. The needle carrier can be received on the membrane in a sealed manner. In one embodiment, a restoring force for the needle can be provided with the aid of the membrane formed from resilient material for retrieval after the extension motion. The resilient membrane is stretched as the needle is extended and then draws the needle back again. This restoring force can retract the needle either alone or in combination with other return mechanisms.

The piercing depth adjuster may be fixable in one or more axial displacement positions relative to the tip of the needle. For example, different latched positions of the piercing depth adjuster can be provided with the axial displacement.

The above descriptions of embodiments apply accordingly to the needle module or piercing element module. In one embodiment, a needle module for a hand-held device for piercing a human or animal skin is provided and has the following features: a module housing, a coupling portion, which is formed on the module housing in order to be coupled to a housing of a drive device, a piercing device, which is formed in the module housing with a needle and can be coupled directly or, via a coupling device, indirectly to the drive device in such a way that, to move the needle axially with respect to the module housing, a feed motion provided by the drive device can be introduced onto the piercing device, a module housing opening, relative to which the needle moves forwards and backwards during operation, and a piercing depth adjuster, which is coupled to the piercing device and is entrained with the needle as the needle moves forwards/backwards during operation. A free needle length may be adjusted by arranging the piercing depth adjuster coaxially with the needle and displaceably relative to the needle tip.

BRIEF DESCRIPTION OF THE DRAWINGS

Further exemplary embodiments will be explained in greater detail hereinafter with reference to figures of a drawing, in which.

DETAILED DESCRIPTION OF PREFERRED EMBODIMENTS

FIGS. 1a to 1d each show a schematic illustration of a hand-held device for piercing a human or animal skin, the device being formed in a modular manner in the illustrated embodiment and comprising a housing 1, which is a multi-piece housing in the shown embodiment and comprises a drive device 2 and a needle module 3. The drive device 2 is suitable for repeatedly providing a feed motion, for example by means of an electric motor or manually, the feed motion then being coupled directly or indirectly via a coupling device (not illustrated) into a piercing device in the needle module 3 in order to repeatedly extend a needle or a piercing element of the piercing device.

A grip piece 3a is connected detachably or non-detachably to the needle module 3 and/or the drive device 2, wherein parts of the drive device 2 and/or of a coupling mechanism for transmission of the drive motion may extend in the grip piece 3a.

Figure 1A:
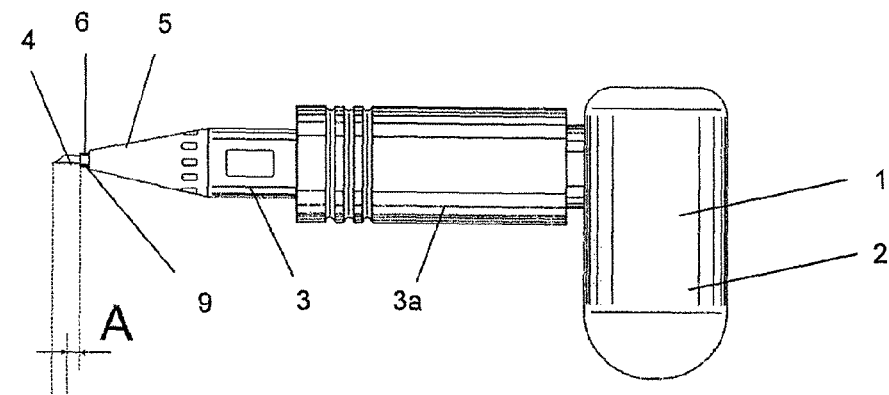
FIGS. 1a to 1d show a schematic illustration of a hand-held device for piercing a human or animal skin.
Figure 1B:
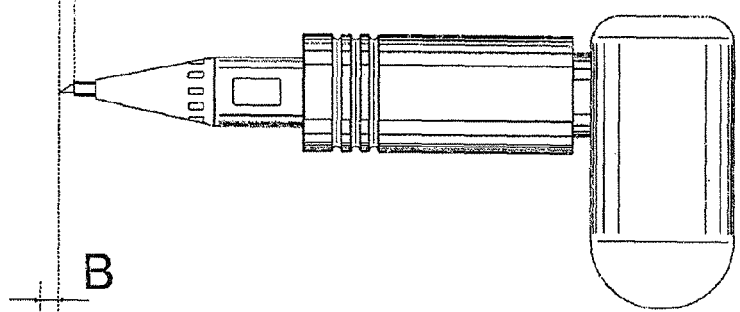
Figure 1C:
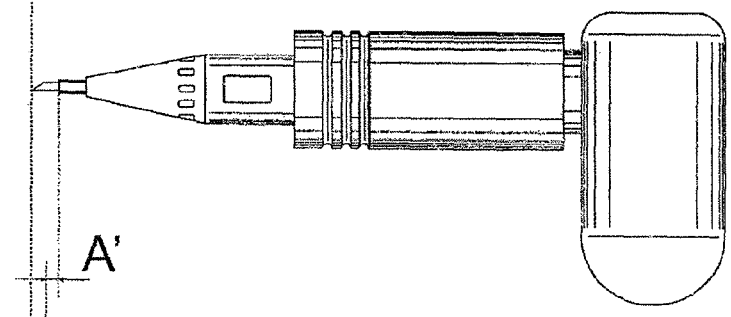
Figure 1D:
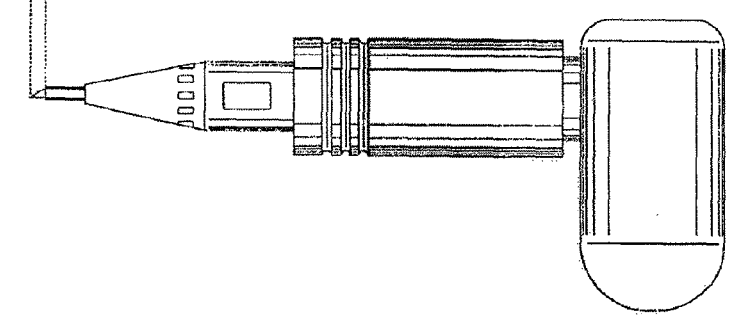

A needle 4, which is part of a piercing or needle device, extends in a front housing portion forming a needle jet 5 and exits through an opening 6 at least when piercing the skin. FIG. 1a to 1d show the needle 4 in a partially or fully extended position, in which the skin is pierced. As the needle is extended, the piercing depth adjuster 9 is entrained with the needle. The protrusion of the needle 4 beyond the front end of the piercing depth adjuster 9 (free needle length) determines the piercing depth into the skin. It can be seen that the piercing depth in the embodiments in FIGS. 1a and 1c are greater than in the embodiments in FIGS. 1b and 1d.

Figure 2:
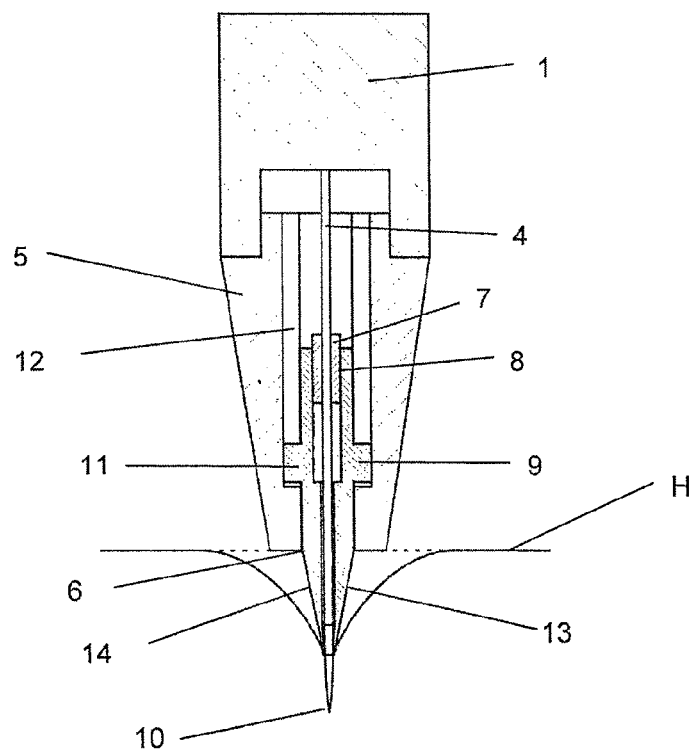
FIG. 2 shows a schematic illustration of a front portion of the hand-held device with a first piercing depth adjustment.
Figure 3:
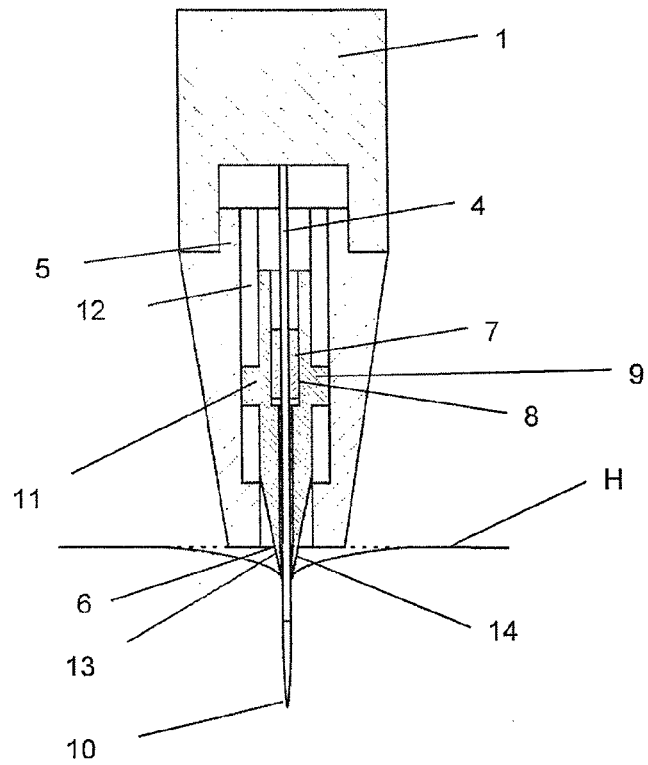
FIG. 3 shows a schematic illustration of a front portion of the hand-held device with a second piercing depth adjustment.

FIGS. 2 and 3 show a front housing portion of the hand-held device from FIG. 1 in cross section. The needle 4 extends in the needle jet 5 and exits in the shown embodiment through the opening 6 at least as the skin is pierced. Both FIG. 2 and FIG. 3 show the needle 4 in an extended position, in which the skin H is pierced to different depths.

A needle ram 7 is arranged on the needle 4 and is coupled via a screw thread 8 to a piercing depth adjuster 9. The axial position of the piercing depth adjuster 9 relative to the tip 10 of the needle 4 (needle protrusion) can be adjusted by rotating the piercing depth adjuster 9. In the illustrated embodiment, this is achieved in that the front housing portion, by means of which the needle jet 5 is formed, is rotatably mounted and guide elements 11 formed on the piercing depth adjuster 9 are mounted in an assigned guide 12 of the needle jet, whereby the piercing depth adjuster 9 is entrained as the needle jet is rotated, whereupon the axial position of the piercing depth adjuster with respect to the needle tip 10 changes.

A distal end portion 13 of the piercing depth adjuster 9 has a conical shaping with an outer surface 14, against which the skin rests during the piercing process.

The different piercing depth in the embodiments in FIGS. 2 and 3 is determined by the position of the piercing depth adjuster 9 relative to the needle tip 10.

Figure 4:
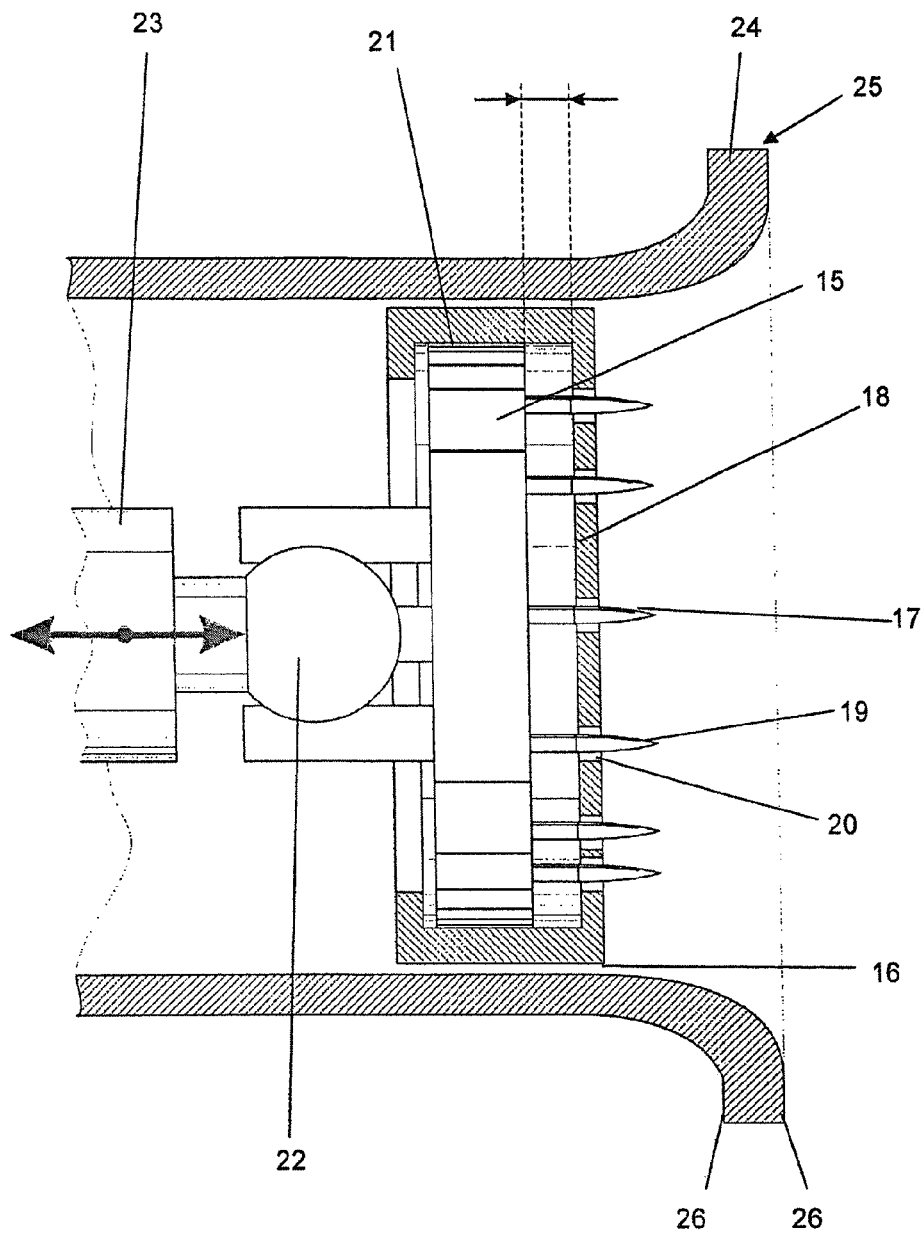
FIG. 4 shows a schematic illustration of a front portion of a hand-held device for piercing a skin.

FIG. 4 shows a schematic illustration of a front portion of a needle module for a hand-held device for piercing a skin, in which, in contrast to the previous embodiments, the piercing device or needle device now comprises a needle plate 15 instead of the needle 4, the needle plate being moved forwards and backwards in an opening 16 during operation. A plurality of needles 17 are arranged on the front face of the needle plate 15. A piercing depth adjuster 18 is also received on the needle plate 15 and is displaceable in the axial direction relative to the needle plate 15, for example since the piercing depth adjuster 18 is received rotatably on the needle plate 15 via a threaded connection 21, and therefore a protrusion 19 (free needle length) of the needles 17 beyond openings 20 is adjustable in order to vary a piercing depth. During operation, the needle plate 15 and also the piercing depth adjuster 18 are then moved forwards and backwards jointly.

In the illustrated embodiment, the needle plate 15 is received via a ball-and-socket joint 22 on a needle plate ram 23, whereby the needle plate 15 can be tilted relative to the needle ram 23.

During operation, a front housing portion 24 is placed via the end face 25 against the skin to be pierced. The needle plate 15 is then moved forwards and backwards together with the piercing depth adjuster 18 in such a way that the needle tips penetrate the skin.

Corners 26 and/or edges on the front housing portion 24 may be rounded.

The features disclosed in the above description, the claims and the drawing may be significant, both individually and in any combination, for the implementation of the various embodiments.

What is claimed is:

1. A needle module for a hand-held device for piercing a human or animal skin, comprising:
    a module housing,
    a coupling portion, which is formed on the module housing in order to be coupled to a housing of a drive device,
    a piercing device, which is formed in the module housing with a needle and can be coupled directly or, via a coupling device, indirectly to the drive device in such a way that a feed motion provided by the drive device can be introduced onto the piercing device,
    a front portion of the housing forming a needle jet and defining a housing opening, wherein the needle and the housing opening are arranged such that the needle moves, during operation, forwards and backwards relative to the housing opening, and
    a piercing depth adjuster, which is coupled to the piercing device in such a way that the piercing depth adjuster is displaceable relative to a tip of the needle and is entrained with the needle as said needle moves forwards and backwards during operation,
    wherein a distal end face of the piercing depth adjuster, in an operating position, forms a common stop face with a front end face of the needle jet, and
    wherein a protrusion of the needle beyond the distal end face of the piercing depth adjuster is adjustable by displacing the piercing depth adjuster relative to the tip of the needle.

2. The needle module according to claim 1, wherein the needle is received on a needle carrier, which is coupled directly or, via the coupling device, indirectly to the drive device.

3. The needle module according to claim 1, wherein the piercing depth adjuster is received on the needle so as to be displaceable in the axial direction.

4. The needle module according to claim 1, wherein the piercing depth adjuster is received on the needle on a needle ram so as to be displaceable in the axial direction.

5. The needle module according to claim 1, wherein the piercing depth adjuster is coupled via a rotary adjustment mechanism to the piercing device.

6. The needle module according to claim 1, wherein a guide element formed on the piercing depth adjuster is assigned a guide formed on the needle jet, the guide element being guided in said guide as the needle moves forwards and backwards during operation.

7. The needle module according to claim 1, wherein a needle jet housing component of the needle jet is arranged displacably on the housing and is functionally coupled to the piercing depth adjuster in such a way that the piecing depth adjuster is displaced in the axial direction relative to the needle tip by displacement of the needle jet housing component.

8. The needle module according to claim 7, wherein the needle jet housing component is arranged rotatably on the housing.

9. The needle module according to claim 1, wherein at least a distal end of the piercing depth adjuster surrounds the needle at least in portions.

10. The needle module according to claim 1, wherein the distal end of the piercing depth adjuster comprises a tapering end portion.

11. The needle module according to claim 1, wherein the needle device and the piercing depth adjuster of the needle module are arranged detachably on the housing of the drive device.

12. The needle module according to claim 1, wherein the piercing depth adjuster can be fixed in one or more axial displacement positions relative to the tip of the needle.

13. The needle module according to claim 1, wherein a free needle length can be set for the needle by arranging the piercing depth adjuster coaxially with the needle and displaceably relative to the needle tip.

14. The needle module according to claim 1, wherein a free needle length is adjustable by moving the piercing depth adjuster into a relative position with reference to the needle tip.

15. The needle module according to claim 1, wherein the drive device is arranged in the housing and is suitable for repeatedly providing a feed motion to the piercing device.

* * * * *